(12) United States Patent
Gysling et al.

(10) Patent No.: US 7,430,924 B2
(45) Date of Patent: Oct. 7, 2008

(54) FLOW MEASUREMENT APPARATUS HAVING STRAIN-BASED SENSORS AND ULTRASONIC SENSORS

(75) Inventors: Daniel L. Gysling, Glastonbury, CT (US); Robert Maron, Middletown, CT (US); Christian O'Keefe, Durham, CT (US)

(73) Assignee: Expro Meters Inc., Wallingford, CT (US)

( * ) Notice: Subject to any disclaimer, the term of this patent is extended or adjusted under 35 U.S.C. 154(b) by 0 days.

(21) Appl. No.: 11/770,048

(22) Filed: Jun. 28, 2007

(65) Prior Publication Data

US 2008/0022782 A1    Jan. 31, 2008

Related U.S. Application Data

(63) Continuation of application No. 10/964,043, filed on Oct. 12, 2004, now Pat. No. 7,237,440.

(60) Provisional application No. 60/510,218, filed on Oct. 10, 2003.

(51) Int. Cl.
*G01F 1/00* (2006.01)
(52) U.S. Cl. ...................................................... 73/861
(58) Field of Classification Search . 73/826.25–861.29, 73/645, 61.41
See application file for complete search history.

(56) References Cited

U.S. PATENT DOCUMENTS

| | | | |
|---|---|---|---|
| 2,874,568 A | 2/1959 | Petermann | |
| 3,715,709 A | 2/1973 | Zacharias et al. | |
| 3,751,979 A | 8/1973 | Ims | |
| 3,781,895 A | 12/1973 | Monser | |
| 3,851,521 A | 12/1974 | Ottenstein | |
| 3,885,432 A | 5/1975 | Herzl | |
| 3,952,578 A | 4/1976 | Jacobs | |
| 4,004,461 A | 1/1977 | Lynworth | |

(Continued)

FOREIGN PATENT DOCUMENTS

DE    4306119    9/1994

(Continued)

OTHER PUBLICATIONS

U.S. Appl. No. 11/964,043.*

(Continued)

*Primary Examiner*—Jewel V Thompson

(57) ABSTRACT

A flow measurement apparatus is provided that combines the functionality of an apparatus that uses strain-based sensors and ultrasonic sensors to measure the speed of sound propagating through a fluid flowing within a pipe, and measure pressures disturbances (e.g. vortical disturbances or eddies) moving with a fluid to determine respective parameters of the flow propagating through a pipe. The apparatus includes a sensing device that includes an array of pressure sensors used to measure the acoustic and convective pressure variations in the flow to determine desired parameters and an ultrasonic meter portion to measure the velocity and volumetric flow of the fluid. In response to an input signal or internal logic, the processor can manually or dynamically switch between the pressure sensors and ultrasonic sensors to measure the parameters of the flow. The flow measurement apparatus thereby provides a robust meter capable of measuring fluid flows having a wide range of different characteristics and flows exposed to different environmental conditions.

28 Claims, 8 Drawing Sheets

U.S. PATENT DOCUMENTS

| | | | |
|---|---|---|---|
| 4,032,259 | A | 6/1977 | Brown |
| 4,048,853 | A | 9/1977 | Smith et al. |
| 4,080,837 | A | 3/1978 | Alexander et al. |
| 4,195,517 | A | 4/1980 | Kalinoski et al. |
| 4,248,085 | A | 2/1981 | Coulthard |
| 4,320,659 | A | 3/1982 | Lynnworth et al. |
| 4,445,389 | A | 5/1984 | Potzick et al. |
| 4,520,320 | A | 5/1985 | Potzick et al. |
| 4,561,310 | A | 12/1985 | Barnard et al. |
| 4,677,305 | A | 6/1987 | Ellinger |
| 4,717,159 | A | 1/1988 | Alston et al. |
| 4,896,540 | A | 1/1990 | Shakkottai et al. |
| 4,932,262 | A | 6/1990 | Wlodarczyk |
| 5,040,415 | A | 8/1991 | Barkhoudarian |
| 5,060,506 | A | 10/1991 | Douglas |
| 5,083,452 | A | 1/1992 | Hope |
| 5,218,197 | A | 6/1993 | Carroll |
| 5,285,675 | A | 2/1994 | Colgate et al. |
| 5,289,726 | A | 3/1994 | Miau et al. |
| 5,359,897 | A | 11/1994 | Hamstead et al. |
| 5,363,342 | A | 11/1994 | Layton et al. |
| 5,367,911 | A | 11/1994 | Jewell et al. |
| 5,398,542 | A | 3/1995 | Vasbinder |
| 5,524,475 | A | 6/1996 | Kolpak et al. |
| 5,526,844 | A | 6/1996 | Kamen et al. |
| 5,591,922 | A | 1/1997 | Segeral et al. |
| 5,625,140 | A | 4/1997 | Cadet et al. |
| 5,708,211 | A | 1/1998 | Jepson et al. |
| 5,741,980 | A | 4/1998 | Hill et al. |
| 5,770,805 | A | 6/1998 | Castel |
| 5,770,806 | A | 6/1998 | Hiismaki |
| 5,835,884 | A | 11/1998 | Brown |
| 5,845,033 | A | 12/1998 | Berthold et al. |
| 5,856,622 | A | 1/1999 | Yamamoto et al. |
| 5,948,959 | A | 9/1999 | Peloquin |
| 6,016,702 | A | 1/2000 | Maron |
| 6,151,958 | A | 11/2000 | Letton et al. |
| 6,202,494 | B1 | 3/2001 | Ricbel et al. |
| 6,233,374 | B1 | 5/2001 | Ogle et al. |
| 6,261,232 | B1 | 7/2001 | Yokosawa et al. |
| 6,345,539 | B1 | 2/2002 | Rawes et al. |
| 6,349,599 | B1 | 2/2002 | Lynnworth et al. |
| 6,354,147 | B1 | 3/2002 | Gysling et al. |
| 6,378,357 | B1 | 4/2002 | Han et al. |
| 6,397,683 | B1 | 6/2002 | Hagenmeyer et al. |
| 6,412,353 | B1 | 7/2002 | Kleven et al. |
| 6,435,030 | B1 | 8/2002 | Gysling et al. |
| 6,442,996 | B1 | 9/2002 | Thurston et al. |
| 6,443,226 | B1 | 9/2002 | Diener et al. |
| 6,450,037 | B1 | 9/2002 | McGuinn et al. |
| 6,463,813 | B1 | 10/2002 | Gysling |
| 6,532,827 | B1 | 3/2003 | Ohnishi |
| 6,536,291 | B1 | 3/2003 | Gysling et al. |
| 6,550,342 | B2 | 4/2003 | Croteau et al. |
| 6,558,036 | B2 | 5/2003 | Gysling et al. |
| 6,587,798 | B2 | 7/2003 | Kersey et al. |
| 6,601,005 | B1 | 7/2003 | Eryurek et al. |
| 6,601,458 | B1 | 8/2003 | Gysling et al. |
| 6,609,069 | B2 | 8/2003 | Gysling |
| 6,658,945 | B1 | 12/2003 | Kleven |
| 6,672,163 | B2 | 1/2004 | Han et al. |
| 6,691,584 | B2 | 2/2004 | Gysling et al. |
| 6,698,297 | B2 | 3/2004 | Gysling |
| 6,732,575 | B2 | 5/2004 | Gysling et al. |
| 6,773,603 | B2 | 8/2004 | Moorehead et al. |
| 6,782,150 | B2 | 8/2004 | Davis et al. |
| 6,813,962 | B2 | 11/2004 | Gysling et al. |
| 6,837,098 | B2 | 1/2005 | Gysling et al. |
| 6,837,332 | B1 | 1/2005 | Rodney |
| 6,862,920 | B2 | 3/2005 | Gysling et al. |
| 6,889,562 | B2 | 5/2005 | Gysling et al. |
| 6,898,541 | B2 | 5/2005 | Gysling et al. |
| 6,971,259 | B2 | 12/2005 | Gysling |
| 6,988,411 | B2 | 1/2006 | Gysling et al. |
| 7,032,432 | B2 | 4/2006 | Gysling et al. |
| 2002/0123852 | A1 | 9/2002 | Gysling et al. |
| 2002/0129662 | A1 | 9/2002 | Gysling et al. |
| 2003/0038231 | A1 | 2/2003 | Bryant et al. |
| 2003/0089161 | A1 | 5/2003 | Gysling |
| 2003/0136186 | A1 | 7/2003 | Gysling et al. |
| 2003/0154036 | A1 | 8/2003 | Gysling et al. |
| 2004/0006409 | A1 | 1/2004 | Liljenberg et al. |
| 2004/0016284 | A1 | 1/2004 | Glysing et al. |
| 2004/0069069 | A1 | 4/2004 | Gysling et al. |
| 2004/0074312 | A1 | 4/2004 | Gysling |
| 2004/0144182 | A1 | 7/2004 | Gylsing et al. |
| 2004/0167735 | A1 | 8/2004 | Rothman et al. |
| 2004/0168522 | A1 | 9/2004 | Bailey et al. |
| 2004/0168523 | A1 | 9/2004 | Bailey et al. |
| 2004/0194539 | A1 | 10/2004 | Gysling |
| 2004/0199340 | A1 | 10/2004 | Gysling et al. |
| 2004/0199341 | A1 | 10/2004 | Gysling et al. |
| 2004/0210404 | A1 | 10/2004 | Gysling et al. |
| 2004/0226386 | A1 | 11/2004 | Croteau et al. |
| 2004/0231431 | A1 | 11/2004 | Bailey et al. |
| 2004/0255695 | A1 | 12/2004 | Gysling et al. |
| 2005/0000289 | A1 | 1/2005 | Gysling et al. |
| 2005/0005711 | A1 | 1/2005 | Gysling et al. |
| 2005/0005712 | A1 | 1/2005 | Gysling et al. |
| 2005/0005713 | A1 | 1/2005 | Winston et al. |
| 2005/0005912 | A1 | 1/2005 | Gysling et al. |
| 2005/0011258 | A1 | 1/2005 | Gysling et al. |
| 2005/0011283 | A1 | 1/2005 | Gysling et al. |
| 2005/0011284 | A1 | 1/2005 | Davis et al. |
| 2005/0012935 | A1 | 1/2005 | Kersey |
| 2005/0033545 | A1 | 2/2005 | Gysling |
| 2005/0039520 | A1 | 2/2005 | Davis et al. |
| 2005/0044929 | A1 | 3/2005 | Gysling et al. |
| 2005/0044966 | A1 | 3/2005 | Gysling et al. |
| 2005/0050956 | A1 | 3/2005 | Gysling et al. |
| 2005/0061060 | A1 | 3/2005 | Banach et al. |
| 2005/0072216 | A1 | 4/2005 | Engel |
| 2005/0125166 | A1 | 6/2005 | Loose et al. |
| 2005/0171710 | A1 | 8/2005 | Gysling et al. |

FOREIGN PATENT DOCUMENTS

| | | |
|---|---|---|
| EP | 0290336 | 11/1988 |
| EP | 1186868 | 3/2002 |
| GB | 2210169 | 6/1989 |
| WO | WO 93/14382 | 7/1993 |
| WO | WO 99/067629 | 12/1999 |
| WO | WO 00/00793 | 1/2000 |
| WO | WO 00/046583 | 8/2000 |
| WO | WO 01/02810 | 1/2001 |
| WO | WO 02/050511 | 6/2002 |
| WO | WO 2004/063741 | 7/2004 |

OTHER PUBLICATIONS

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attenuation of Acoustic Waves in Suspensions" by R.L. Gibson, Jr. and M.N. Toksoz.

Sonar-Based Volumetric Flow Meter For Pulp and Paper Applications—Daniel L. Gysling & Douglas H. Loose—Dec. 13, 2003.

Sonar-Based Volumetric Flow Meter for Chemical and Petrochemical Applications—Daniel L. Gysling & Douglas H. Loose—Feb. 14, 2003.

New Flowmeter Principle—By Walt Boyes—Flow Control Magazine—Oct. 2003 Issue.

Sonar Gets into the Flow—Daniel L. Gysling and Douglas H. Loose—Modern Process—Jan. 2004.

"Flow Velocity Measurement Using Spatial Filter" Yoshio Kurita, Takaharu Matsumoto, Yukitake Shibata—Nov. 1979.

Piezo Film Sensors Technical Manual—Measurement Specialities Inc.—Sensor Products Division Apr. 2, 1999.

* cited by examiner

US 7,430,924 B2

FLOW MEASUREMENT APPARATUS HAVING STRAIN-BASED SENSORS AND ULTRASONIC SENSORS

CROSS-REFERENCE TO RELATED PATENT APPLICATIONS

This application is a Continuation of U.S. patent application Ser. No. 10/964,043 filed on Oct. 12, 2004, which will issue into U.S. Pat. No. 7,237,440 on Jul. 3, 2007, which claimed the benefit of U.S. Provisional Patent Application No. 60/510,218 filed Oct. 10, 2003, which are incorporated by reference herein in their entirety.

TECHNICAL FIELD

This invention relates to an apparatus for measuring a parameter of a process flow passing within a pipe, and more particularly to a flow measurement apparatus having ultrasonic sensors and an array of strain-based sensors and for processing data signals therefrom to provide an output indicative of the speed of sound propagating through the process flow and/or a flow parameter of the process flow passing through a pipe.

BACKGROUND ART

Ultrasonic flow meters are well known for measuring volumetric flow of liquids and gas. Ultrasonic meters may be mounted within a pipe, mounted within a spool piece, or clamped onto the outer surface of the pipe. While ultrasonic meters are suitable and in some case accurate flow meters, such as gas custody meters, ultrasonic meters are not suitable for all fluid flows. For instance, ultrasonic meters have difficulty measuring volumetric flow rate when measuring aerated fluids. The gas bubbles scatter the ultrasonic waves and therefore, provide an inaccurate or no output at all.

Similarly, an array-based flow meter that uses an array of sensors disposed along the pipe for measuring vortical disturbances and/or acoustic waves propagating through the flow, are suitable for some applications and not as suitable for other applications. The array-based flow meter and the ultrasonic meter have common applications that are both suitable for use, however, in other instances, the ultrasonic meter functions better than the array-based meter in some applications and the array-based flow meter functions better than the ultrasonic meter in other applications. The present invention combines the two technologies into a single flow meter to provide a flow meter capable of functions in a great number of applications than each flow meter can function alone.

SUMMARY OF THE INVENTION

Objects of the present invention include providing a flow measuring apparatus having a dual function of measuring the parameters of the fluid flow using an array of strain-based sensor and/or ultrasonic sensors to provide a more robust flow measuring apparatus for flows of varying characteristics and process environments.

In one aspect of the present invention, an apparatus for measuring a process flow flowing within a pipe is provided. The apparatus includes at least two strain sensors disposed at different axial locations along the pipe. Each of the strain sensors provides a respective pressure signal indicative of a pressure disturbance within the pipe at a corresponding axial position. At least one ultrasonic sensor is disposed on the pipe that provide a signal indicative of a parameter of the process flow. A signal processor, responsive to said pressure signals and ultrasonic signal, provides a first signal indicative of a velocity of a pressure field moving with the process flow and/or provides a second signal indicative of a speed of sound propagating through the process flow.

The foregoing and other objects, features and advantages of the present invention will become more apparent in light of the following detailed description of exemplary embodiments thereof.

BEST MODE FOR CARRYING OUT THE INVENTION

Figure 1:
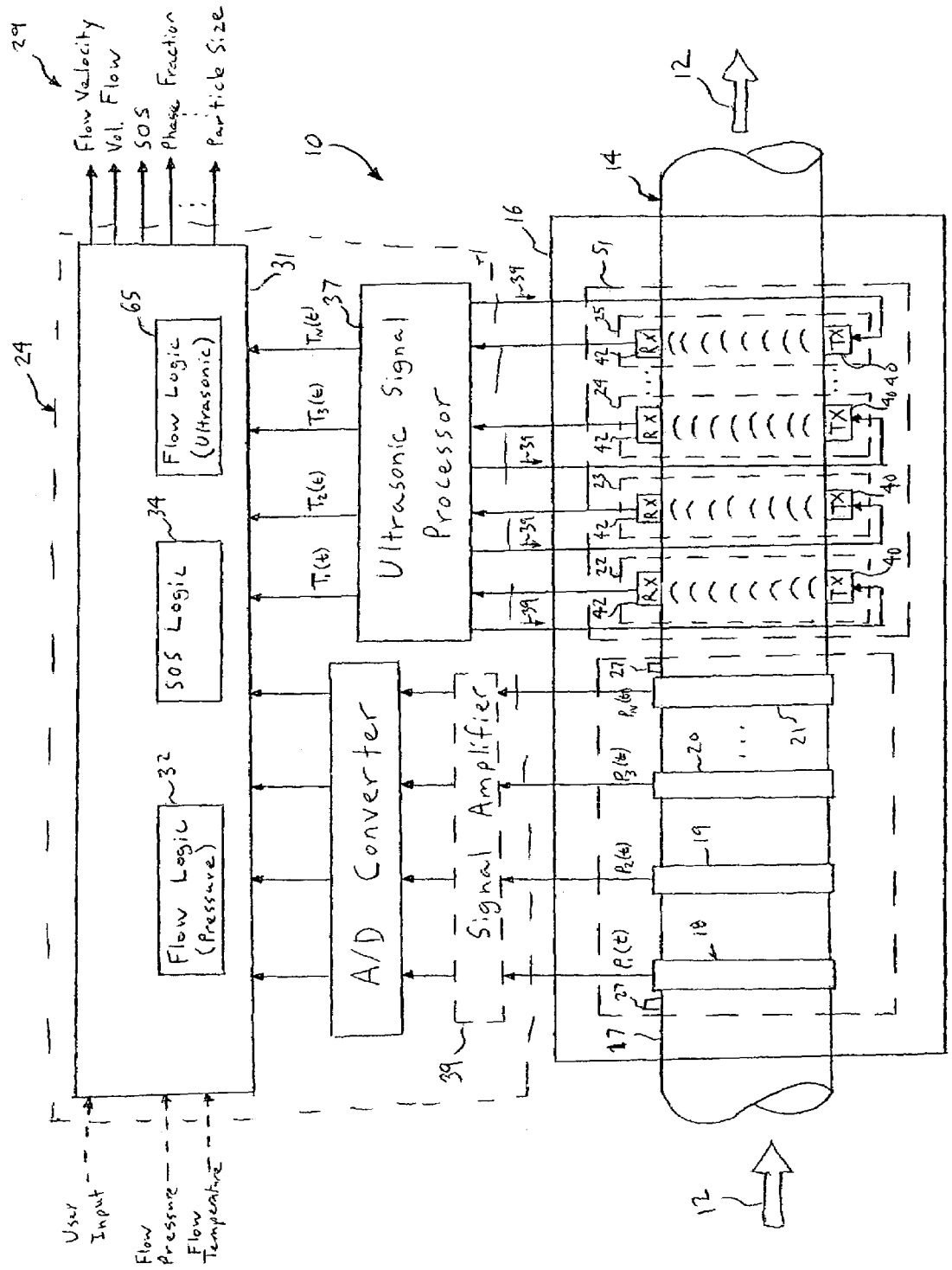
FIG. 1 is a schematic diagram of a flow measurement apparatus having an array of strain-based sensors and an array of ultrasonic sensors for providing a dual function in accordance with the present invention.

FIG. 1 illustrates a schematic diagram of a flow measurement apparatus 10 that includes a sensing device (sensor head) 16 mounted to a pipe 14 and a processing unit or array processor (transmitter) 24. The apparatus 10 measures a characteristic or parameter of a single phase fluid (e.g., gas and liquid) and/or multiphase fluids 12 (e.g., gas/liquid mixtures, liquid/solid mixtures, gas/solid mixtures, steam, pulp and paper slurries, and aerated liquids and mixtures) flowing through the pipe 14. Specifically, the flow characteristics and flow parameters determined include the volumetric flow of the fluid, the consistency or composition of the fluid, the density of the fluid, the Mach number of the fluid, the size of particle flowing through the fluid, the air/mass ratio of the fluid, velocity of the flow, volumetric flow rate, gas volume fraction of the flow, the speed of sound propagating through the flow, and/or the percentage of entrained air within a liquid or slurry.

For instance, the apparatus 10, in accordance with the present invention, can determine the speed at which sound (i.e., acoustic wave 90 in FIG. 2) propagates through the fluid flow 12 within a pipe 14 to measure particular characteristics of the single or multi-phase fluids. The apparatus may also determine the speed at which pressure disturbances propagate through the pipe 14 to determine the velocity of the fluid flow 12. The pressure disturbances may be in the form of vortical disturbances 88 (e.g., turbulent eddies FIG. 2) or other pressure disturbances that convect (or propagate) with the flow. To simplify the explanation of the present invention, the flow propagating through the pipe will be referred to as a process flow with the understanding that the fluid or process flow 12 may be a single phase or multi-phase flow, as described hereinbefore.

The sensing device 16 comprises an array of strain-based sensors or pressure sensors 18-21 for measuring the unsteady pressures produced by vortical disturbances within the pipe and/or speed of sound propagating through the flow, which are indicative of parameters and/or characteristics of the process flow 12. The sensing device 16 further includes an array of ultrasonic sensors 22-23, each of which having a transmitter 40 and a receiver 42, to also measure a parameter of the flow 12.

The pressure signals $P_1(t)$-$P_N(t)$ and ultrasonic signals $S_1(t)$-$S_N(t)$ are provided to the processing unit 24, which digitizes the signals and computes the appropriate flow parameter(s). A cable electronically connects the sensing device 16 to the processing unit 24. The analog pressure sensor signals $P_1(t)$-$P_N(t)$ are typically 4-20 mA current loop signals.

The measurement apparatus 10 may be programmed to provide a flow output parameter 29 corresponding to the pressure signals and/or ultrasonic signals in response to an input/command from an external source, such as control system (not shown) or a user. This capability enables a user to selectively process the input pressure and ultrasonic signals to provide an accurate measurement of the fluid flow 12. For example, the output measurements 29 may be determined using the pressure signals of the pressure sensors 18-21 for conditions when the fluid flow is aerated. In another example, the output measurements 29 may be determined using the ultrasonic signals of the ultrasonic sensors 22-25 when the fluid flow has no or very little entrained gas, and/or when the pipe is vibrating at a relatively high level. As one skilled in the art can appreciate, the present invention allows a user to install one meter on the pipe and measure parameters of the flow under different operating conditions and flow conditions. The configuration of the apparatus may be static, in other words set by the user at installation, or dynamic wherein the user or control system may dynamic switch between (or simultaneously measure) the ultrasonic sensors and the pressure sensors. The processing unit 24 may also provide intelligence that will switch between utilization of the pressure sensors and ultrasonic sensors when sensing degradation of the output measurement or other external parameter (e.g., vibration).

The array of pressure sensors 18-21 comprises an array of at least two pressure sensors 18,19 spaced axially along the outer surface 17 of the pipe 14, having a process flow 12 propagating therein. The pressure sensors 18-21 may be clamped onto or generally removably mounted to the pipe by any releasable fastener, such as bolts, screws and clamps.

Alternatively, the sensors may be permanently attached to or integral (e.g., embedded) with the pipe 14. The array of sensors of the sensing device 16 may include any number of pressure sensors 18-21 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the flow. Therefore, the number of sensors used is dependent at least on the degree of accuracy desired and the desired update rate of the output parameter provided by the apparatus 10. The pressure sensors 18-19 measure the unsteady pressures produced by acoustic waves propagating through the flow and/or pressure disturbances (e.g., vortical eddies) that convect with the flow within the pipe 14, which are indicative of the SOS propagating through the fluid flow 12 in the pipe and the velocity of disturbances propagating through the flow 12 of the mixture 12, respectively. The output signals ($P_1(t)$-$P_N(t)$) of the pressure sensors 18-21 are provided to a signal amplifier 39 that amplifies the signals generated by the pressure sensors 18-21. The processing unit 24 processes the pressure measurement data $P_1(t)$-$P_N(t)$ and determines the desired parameters and characteristics of the flow 12, as described hereinbefore.

The apparatus 10 also contemplates providing one or more acoustic sources 27 to enable the measurement of the speed of sound propagating through the flow for instances of acoustically quiet flow. The acoustic source may be a device that taps or vibrates on the wall of the pipe, for example. The acoustic sources may be disposed at the input end of output end of the array of sensors 18-21, or at both ends as shown. One should appreciate that in most instances the acoustics sources are not necessary and the apparatus passively detects the acoustic ridge provided in the flow 12, as will be described in greater detail hereinafter. The passive noise includes noise generated by pumps, valves, motors, and the turbulent mixture itself.

As suggested and further described in greater detail hereinafter, the apparatus 10 has the ability to measure the speed of sound (SOS) and flow rate (or velocity) using one or both of the following techniques described herein below:

1) Determining the speed of sound of acoustical disturbances or sound waves propagating through the flow 12 using the array of pressure sensors 18-21, and/or
2) Determining the velocity of pressure disturbances (e.g., vortical eddies) propagating through the flow 12 using the array of pressure sensors 18-21.

Generally, the first technique measures unsteady pressures created by acoustical disturbances propagating through the flow 12 to determine the speed of sound (SOS) propagating through the flow. Knowing the pressure and/or temperature of the flow and the speed of sound of the acoustic disturbances or waves, the processing unit 24 can determine the volumetric flow of the fluid, the consistency or composition of the fluid, the density of the fluid, the Mach number of the fluid, the average size of particles flowing through the fluid, the air/mass ratio of the fluid, and/or the percentage of entrained air within a liquid or slurry, such as that described in U.S. patent application Ser. No. 10/349,716, filed Jan. 23, 2003, U.S. patent application Ser. No. 10/376,427, filed Feb. 26, 2003, U.S. patent application Ser. No. 10/762,410, filed Jan. 21, 2004, which are all incorporated by reference.

Figure 2:
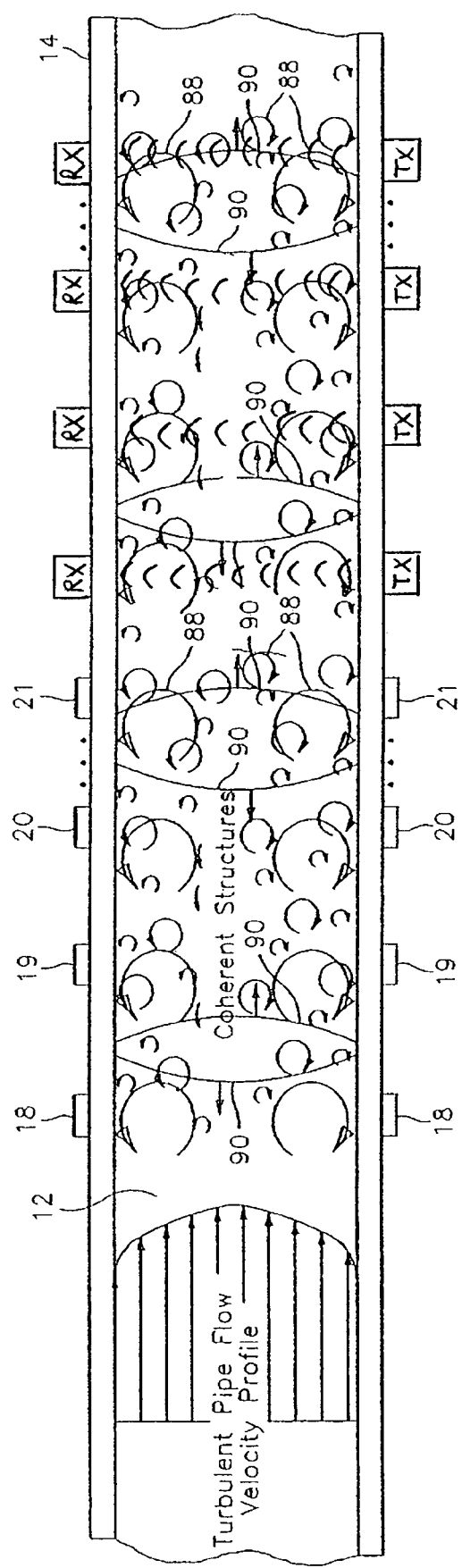
FIG. 2 is a cross-sectional view of a pipe having a turbulent fluid flow or mixture flowing therein, the flow having coherent structures therein, namely acoustic waves and vortical disturbances, in accordance with the present invention.

The second technique measures the velocities associated with unsteady flow fields and/or pressure disturbances, such as that created by vertical disturbances or "eddies" 88 (see FIG. 2), that convect with the process flow 12 to determine the velocity of the process flow. The pressure sensors 18-21 measure the unsteady pressures $P_1$-$P_N$ created by the vortical disturbances 88, for example, as these disturbances convect with the flow 12 through the pipe 14 in a known manner, as shown in FIG. 2. Therefore, the velocity of these vortical disturbances is related to the velocity of the flow 12 and hence the volumetric flow rate may be determined, as will be described in greater detail hereinafter.

As shown in FIG. 1, the present invention contemplates a flow measurement apparatus 10 that combines the functionality of an apparatus for measuring the velocity of the process flow and an apparatus for measuring the speed of sound propagating through the flow within a pipe. The pressure signals $P_1(t)$-$P_N(t)$ of the array of sensors 18-21 of the sensing device 16 are provided to an array processor 31 that includes flow logic 32 for determining the velocity and/or the volumetric flow of the fluid 12 and includes speed of sound (SOS) logic 34 for determining the composition of the flow, the average size of particles within the flow, the air/mass ratio of the flow, phase fraction of the flow, and/or the speed of sound propagating through the flow.

As shown in FIG. 2, an apparatus 10 embodying the present invention has an array of at least two strain-based or pressure sensors 18,19, located at two locations $x_1,x_2$ axially along the pipe 14 for sensing respective stochastic signals propagating between the sensors 18,19 within the pipe at their respective locations. Each sensor 18,19 provides a signal indicating an unsteady pressure at the location of each sensor, at each instant in a series of sampling instants. One will appreciate that the sensor array may include more than two pressure sensors as depicted by pressure sensor 20,21 at location $x_3,x_N$. The pressure generated by the convective pressure disturbances (e.g., eddies 88) and acoustic waves 90 (see FIG. 2) may be measured through strained-based sensors and/or pressure sensors 18-21. The pressure sensors 18-21 provide analog pressure time-varying signals $P_1(t),P_2(t),P_3(t),P_N(t)$ to the signal processing unit 24

Figure 3:
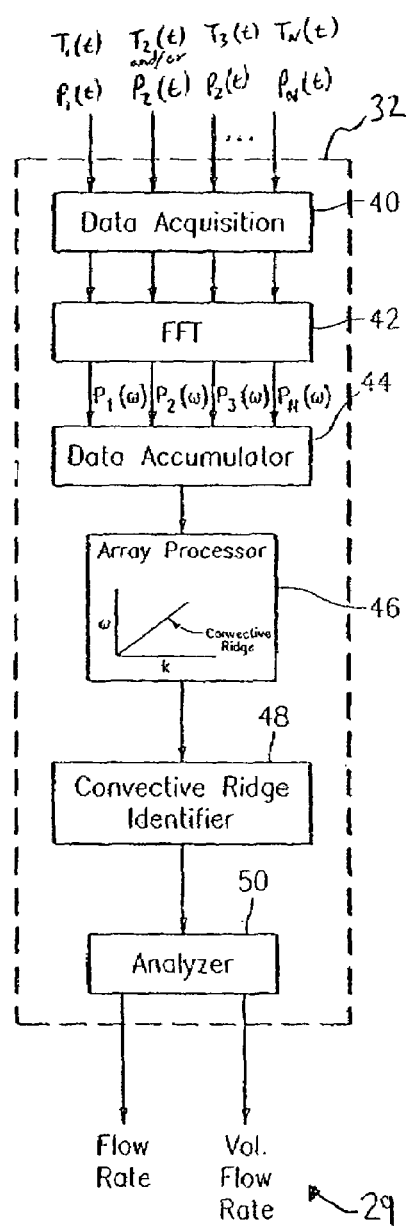
FIG. 3 is a schematic diagram of a flow logic of an array processor of a flow measuring apparatus in accordance with the present invention.

The Flow Logic 32 of the processing unit 24 as shown in FIG. 3 receives the pressure signals from the array of sensors 18-21. A data acquisition unit 40 (e.g., A/D converter) converts the analog signals to respective digital signals. The digitized signals are provided to Fast Fourier Transform (FFT) logic 42. The FFT logic calculates the Fourier transform of the digitized time-based input signals $P_1(t)$-$P_N(t)$ and provides complex frequency domain (or frequency based) signals $P_1(\omega), P_2(\omega), P_3(\omega), P_N(\omega)$ indicative of the frequency content of the input signals. Instead of FFT's, any other technique for obtaining the frequency domain characteristics of the signals $P_1(t)$-$P_N(t)$, may be used. For example, the cross-spectral density and the power spectral density may be used to form one or more frequency domain transfer functions (or frequency responses or ratios) discussed hereinafter.

One technique of determining the convection velocity of the turbulent eddies 88 within the process flow 12 is by characterizing a convective ridge of the resulting unsteady pressures using an array of sensors or other beam forming techniques, similar to that described in U.S. Pat. No. 6,889,526 and U.S. Pat. No. 6,609,069, which are incorporated herein by reference.

A data accumulator 44 accumulates the frequency signals $P_1(\omega)$-$P_N(\omega)$ over a sampling interval, and provides the data to an array processor 46, which performs a spatial-temporal (two-dimensional) transform of the sensor data, from the xt domain to the k-ω domain, and then calculates the power in the k-ω plane, as represented by a k-ω plot.

The array processor 46 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length.

Convective characteristics or parameters have a dispersion relationship that can be approximated by the straight-line equation, $$k=\omega/u,$$

where u is the convection velocity (flow velocity). A plot of k-ω pairs is obtained from a spectral analysis of sensor samples associated with convective parameters. The pairings are portrayed so that the energy of the disturbance spectrally corresponding to the pairings can be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 88 are distributed over a range of length scales and hence temporal frequencies.

To calculate the power in the k-ω plane, as represented by a k-ω plot (see FIG. 5) of either the signals, the array processor 46 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 18-21.

The present invention may use temporal and spatial filtering to precondition the signals to effectively filter out the common mode characteristics $P_{common\ mode}$ and other long wavelength (compared to the sensor spacing) characteristics in the pipe 14 by differencing adjacent sensors and retaining a substantial portion of the stochastic parameter associated with the flow field and any other short wavelength (compared to the sensor spacing) low frequency stochastic parameters.

Figure 5:
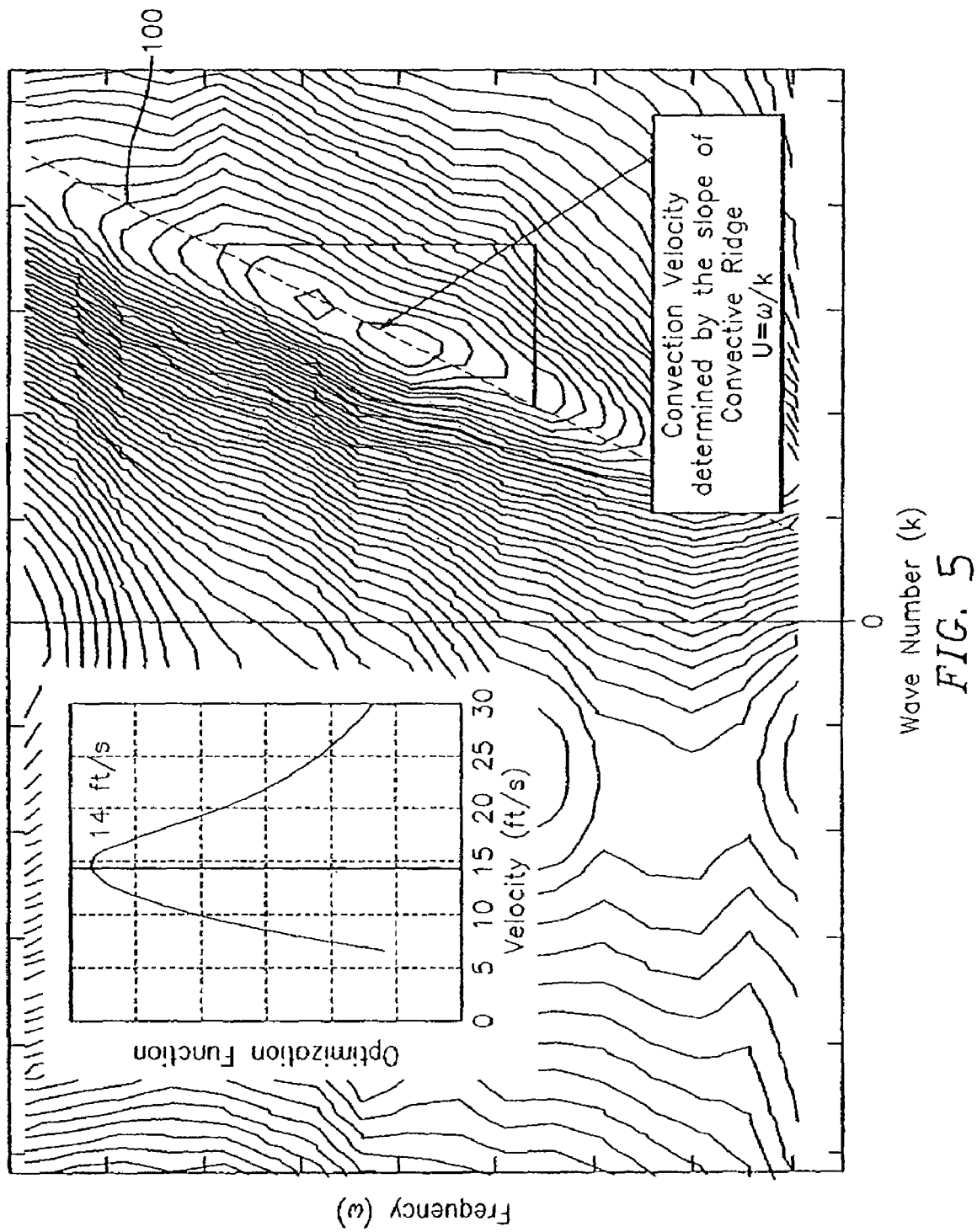
FIG. 5 is a k$\omega$ plot of data processed from an apparatus embodying the present invention that illustrates the slope of a convective ridge, and a plot of the optimization function of the convective ridge, in accordance with the present invention.

In the case of suitable turbulent eddies 88 (see FIG. 2) being present, the power in the k-ω plane shown in a k-ω plot of FIG. 5 shows a convective ridge 100. The convective ridge represents the concentration of a stochastic parameter that convects with the flow and is a mathematical manifestation of the relationship between the spatial variations and temporal variations described above. Such a plot will indicate a tendency for k-ω pairs to appear more or less along a line 100 with some slope, the slope indicating the flow velocity.

Once the power in the k-ω plane is determined, a convective ridge identifier 48 uses one or another feature extraction method to determine the location and orientation (slope) of any convective ridge 100 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 48 provides information about the different trial convection velocities, information referred to generally as convective ridge information.

The analyzer 50 examines the convective ridge information including the convective ridge orientation (slope). Assuming the straight-line dispersion relation given by k=ω/u, the analyzer 50 determines the flow velocity, Mach number and/or volumetric flow. The volumetric flow is determined by multiplying the cross-sectional area of the inside of the pipe with the velocity of the process flow.

Figure 4:
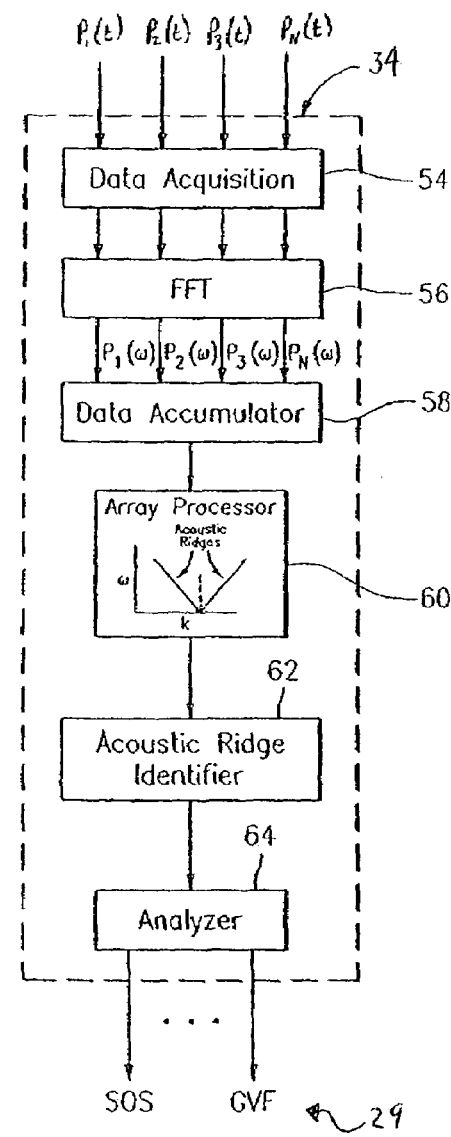
FIG. 4 is a schematic diagram of a speed of sound (SOS) logic of an array processor of a flow measuring apparatus in accordance with the present invention.

As shown in FIG. 4, the SOS Logic 34 includes a second data acquisition unit 54 that digitizes the pressure signals $P_1(t)$-$P_N(t)$ associated with the acoustic waves 14 propagating through the pipe 14. Similar to the FFT logic 42, an FFT logic 56 calculates the Fourier transform of the digitized time-based input signals $P_1(t)$-$P_N(t)$ and provides complex frequency domain (or frequency based) signals $P_1(\omega), P_2(\omega), P_3(\omega), P_N(\omega)$ indicative of the frequency content of the input signals.

A data accumulator 58 accumulates the signals $P_1(t)$-$P_N(t)$ from the sensors, and provides the data accumulated over a sampling interval to an array processor 60, which performs a spatial-temporal (two-dimensional) transform of the sensor data, from the xt domain to the k-ω domain, and then calculates the power in the k-ω plane, as represented by a k-ω plot, similar to that provided by the convective array processor 46.

To calculate the power in the k-ω plane, as represented by a k-ω plot (see FIG. 6) of either the signals or the differenced signals, the array processor 60 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of the array of pressure sensors 18-21.

Figure 6:
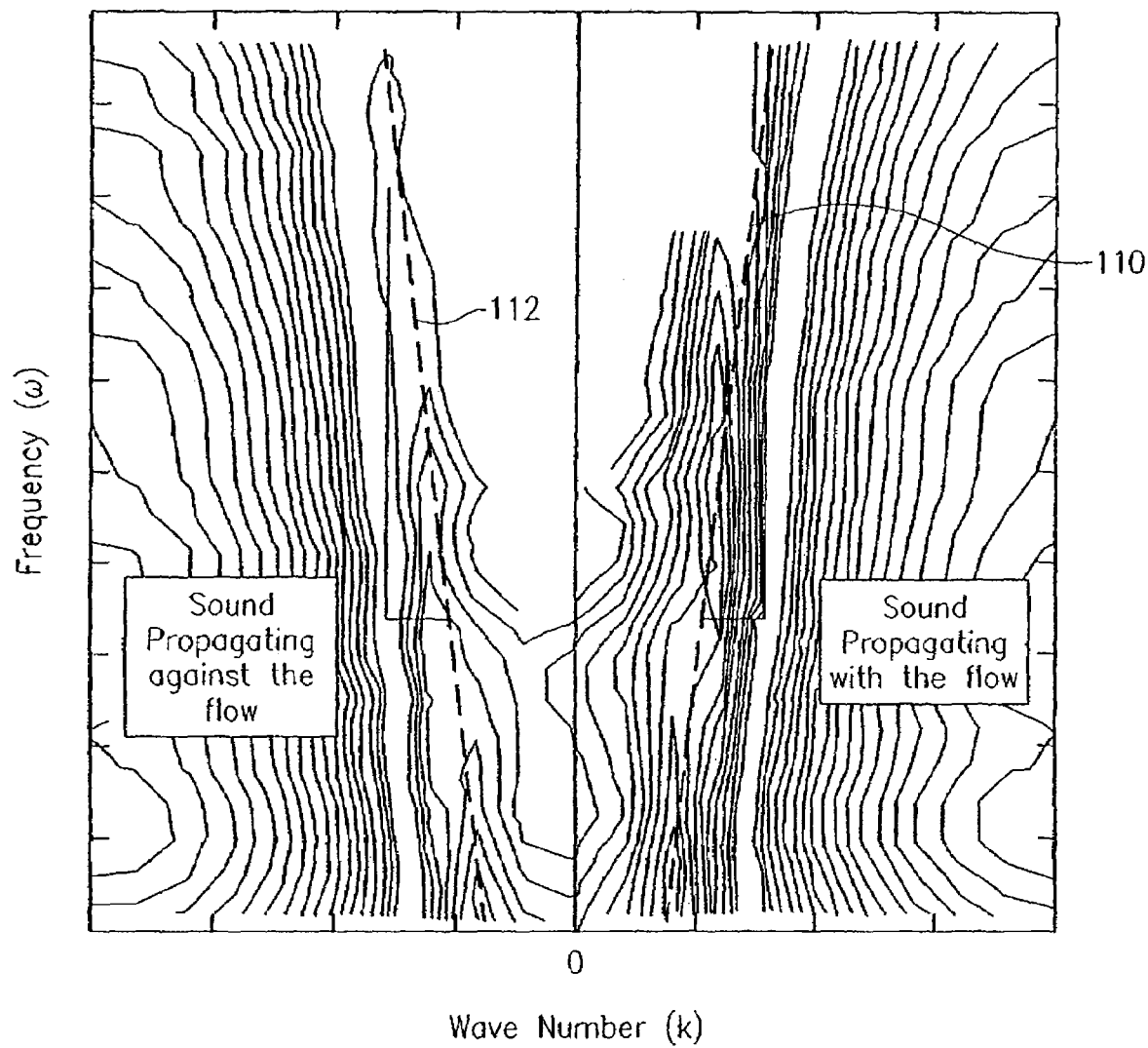
FIG. 6 is a k$\omega$ plot of data processed from an apparatus embodying the present invention that illustrates the slopes of a pair of acoustic ridges, in accordance with the present invention.

In the case of suitable acoustic waves 90 being present in both axial directions, the power in the k-ω plane shown in a k-ω plot of FIG. 6 so determined will exhibit a structure that is called an acoustic ridge 110,112 in both the left and right planes of the plot, wherein one of the acoustic ridges 110 is indicative of the speed of sound traveling in one axial direction and the other acoustic ridge 112 being indicative of the speed of sound traveling in the other axial direction.

The acoustic ridges represent the concentration of a stochastic parameter that propagates through the flow and is a mathematical manifestation of the relationship between the spatial variations and temporal variations described above. Such a plot will indicate a tendency for k-ω pairs to appear more or less along a line 110,112 with some slope, the slope indicating the speed of sound. The power in the k-ω plane so determined is then provided to an acoustic ridge identifier 62, which uses one or another feature extraction method to determine the location and orientation (slope) of any acoustic ridge present in the left and right k-ω plane. The velocity may be determined by using the slope of one of the two acoustic ridges 110,112 or averaging the slopes of the acoustic ridges 110,112.

Finally, information including the acoustic ridge orientation (slope) is used by an analyzer 64 to determine the flow parameters 29 relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

Similar to the array processor 46, the array processor 60 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by k=2π/λ where λ is the wavelength of a spectral component, and corresponding angular frequencies given by ω=2πν.

One such technique of determining the speed of sound propagating through the flow 12 is using array processing techniques to define an acoustic ridge in the k-ω plane as shown in FIG. 6. The slope of the acoustic ridge is indicative of the speed of sound propagating through the flow 12. The speed of sound (SOS) is determined by applying sonar array-ing processing techniques to determine the speed at which the one dimensional acoustic waves propagate past the axial array of unsteady pressure measurements distributed along the pipe 14.

The apparatus 10 of the present invention measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and flow 12 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While the sonar-based flow meter using an array of sensors to measure the speed of sound of an acoustic wave propagating through the mixture is shown and described, one will appreciate that any means for measuring the speed of sound of the acoustic wave may be used to determine the entrained gas volume fraction of the mixture/fluid or other characteristics of the flow described hereinbefore.

The analyzer 64 of the acoustic processing unit 53 provides output signals indicative of characteristics of the process flow 12 that are related to the measured speed of sound (SOS) propagating through the flow 12. For example, to determine the gas volume fraction (or phase fraction), the analyzer 64 assumes a nearly isothermal condition for the flow 12. As such the gas volume fraction or the void fraction is related to the speed of sound by the following quadratic equation:

$$Ax^2+Bx+C=0$$

wherein x is the speed of sound, $A=1+rg/rl*(K_{eff}/P-1)-K_{eff}/P$, $B=K_{eff}/P-2+rg/rl$; $C=1-K_{eff}/rl*a_{meas}\hat{\ }2$); Rg=gas density, rl=liquid density, $K_{eff}$=effective K (modulus of the liquid and pipewall), P=pressure, and $a_{meas}$=measured speed of sound.

Effectively,

Gas Volume Fraction $(GVF)=(-B+\text{sqrt}(B\hat{\ }2-4*A*C))/(2*A)$

Alternatively, the sound speed of a mixture can be related to volumetric phase fraction ($\phi_i$) of the components and the sound speed (a) and densities ($\rho$) of the component through the Wood equation.

$$\frac{1}{\rho_{mix}a^2_{mix\infty}} = \sum_{i=1}^N \frac{\phi_i}{\rho_i a_i^2} \text{ where } \rho_{mix} = \sum_{i=1}^N \rho_i\phi_i$$

One dimensional compression waves propagating within a mixture 12 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{1/a^2_{mix\infty} + \rho_{mix}\frac{2R}{Et}}} \quad (\text{eq 1})$$

Figure 7:
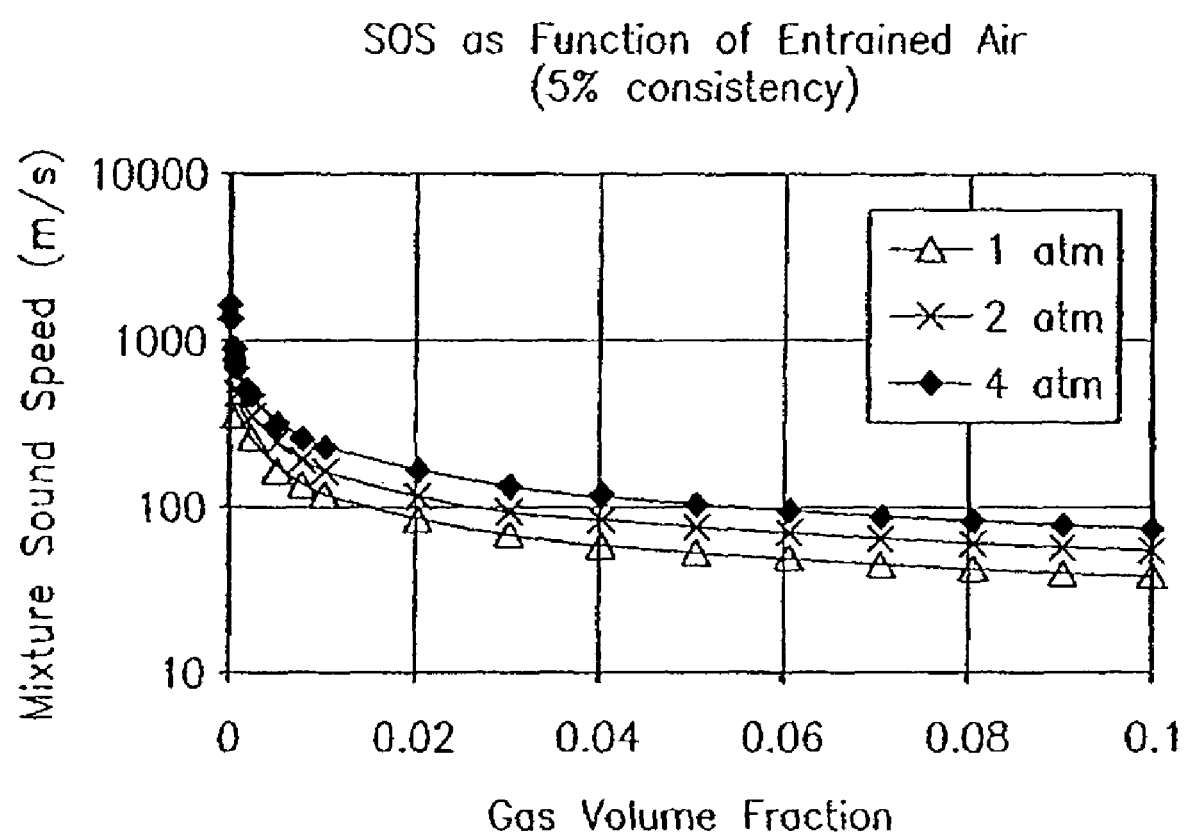
FIG. 7 is a plot of mixture sound speed as a function of gas volume fraction for a 5% consistency slurry over a range of process pressures, in accordance with the present invention.

The mixing rule essentially states that the compressibility of a mixture ($1/(\rho a^2)$) is the volumetrically-weighted average of the compressibilities of the components. For gas/liquid mixtures 12 at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained air volume fraction is shown in FIG. 7.

As described hereinbefore, the apparatus 10 of the present invention includes the ability to accurately determine the average particle size of a particle/air or droplet/air mixture within the pipe 14 and the air to particle ratio. Provided there is no appreciable slip between the air and the solid coal particle, the propagation of one dimensional sound wave through multiphase mixtures is influenced by the effective mass and the effective compressibility of the mixture. For an air transport system, the degree to which the no-slip assumption applies is a strong function of particle size and frequency. In the limit of small particles and low frequency, the no-slip assumption is valid. As the size of the particles increases and the frequency of the sound waves increase, the non-slip assumption becomes increasing less valid. For a given average particle size, the increase in slip with frequency causes dispersion, or, in other words, the sound speed of the mixture changes with frequency. With appropriate calibration the dispersive characteristic of a mixture 12 will provide a measurement of the average particle size, as well as the air to particle ratio (particle/fluid ratio) of the mixture.

In accordance with the present invention the dispersive nature of the system utilizes a first principles model of the interaction between the air and particles. This model is viewed as being representative of a class of models that seek to account for dispersive effects. Other models could be used to account for dispersive effects without altering the intent of this disclosure (for example, see the paper titled "Viscous Attenuation of Acoustic Waves in Suspensions" by R. L. Gibson, Jr. and M. N. Toksöz), which is incorporated herein by reference. The model allows for slip between the local velocity of the continuous fluid phase and that of the particles.

The following relation can be derived for the dispersive behavior of an idealized fluid particle mixture.

$$a_{mix}(\omega) = a_f\sqrt{\frac{1}{1+\frac{\varphi_p\rho_p}{\rho_f\left(1+\omega^2\frac{\rho_p^2 v_p^2}{K^2}\right)}}}$$

In the above relation, the fluid SOS, density ($\rho$) and viscosity ($\phi$) are those of the pure phase fluid, $v_p$ is the volume of individual particles and $\phi_p$ is the volumetric phase fraction of the particles in the mixture.

Figure 8:
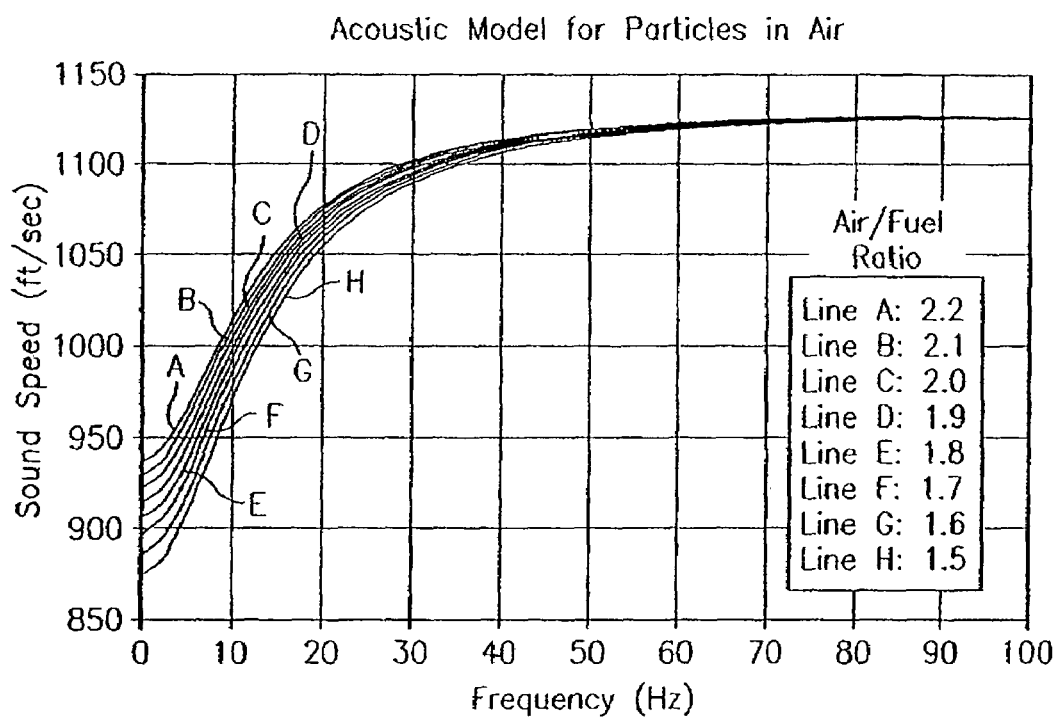
FIG. 8 is a plot of sound speed as a function of frequency for air/particle mixtures with fixed particle size and varying air-to-particle mass ratio in accordance with the present invention.
Figure 9:
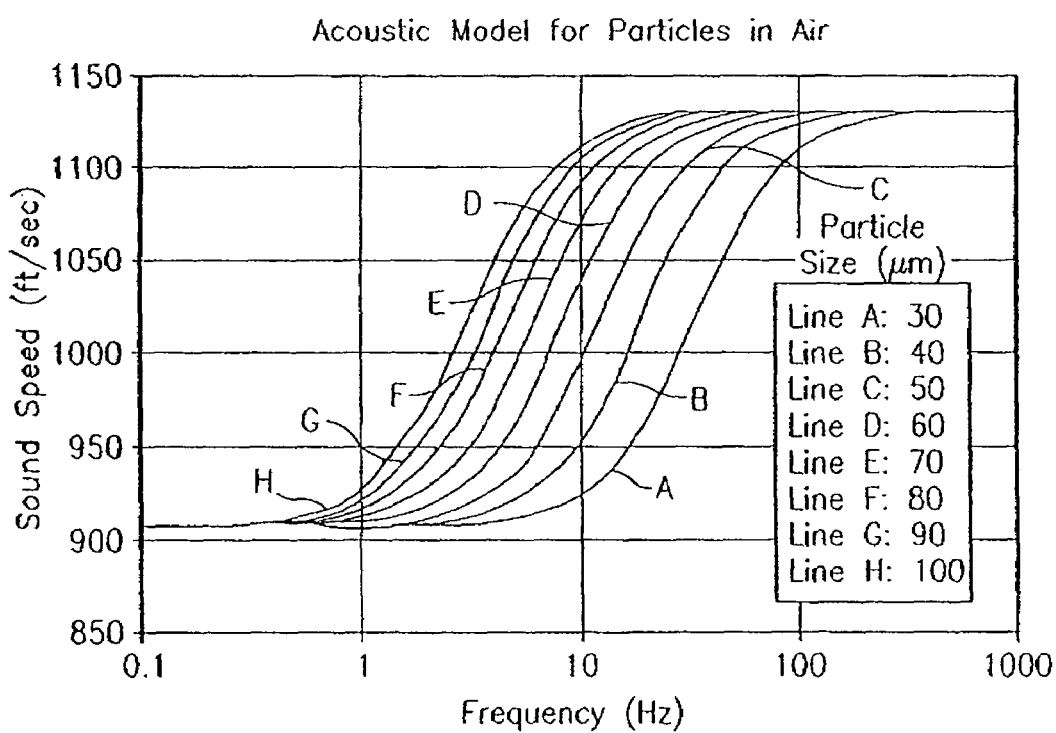
FIG. 9 is a plot of sound speed as a function of frequency for air/particle mixtures with varying particle size where the air-to-particle mass ratio is fixed in accordance with the present invention.

Two parameters of particular interest in steam processes and air-conveyed particles processes are particle size and air-to-fuel mass ratio or steam quality. To this end, it is of interest to examine the dispersive characteristics of the mixture as a function of these two variables. FIGS. 8 and 9 show the dispersive behavior in relations to the speed of sound for coal/air mixtures with parameters typical of those used in pulverized coal deliver systems.

In particular FIG. 8 shows the predicted behavior for nominally 50 µm size coal in air for a range of air-to-fuel ratios. As shown, the effect of air-to-fuel ratio is well defined in the low frequency limit. However, the effect of the air-to-fuel ratio becomes indistinguishable at higher frequencies, approaching the sound speed of the pure air at high frequencies (above ~100 Hz).

Similarly, FIG. 9 shows the predicted behavior for a coal/air mixture with an air-to-fuel ratio of 1.8 with varying particle size. This figure illustrates that particle size has no influence on either the low frequency limit (quasi-steady) sound speed, or on the high frequency limit of the sound speed. However, particle size does have a pronounced effect in the transition region.

FIGS. 8 and 9 illustrate an important aspect of the present invention. Namely, that the dispersive properties of dilute mixtures of particles suspended in a continuous fluid can be broadly classified into three frequency regimes: low frequency range, high frequency range and a transitional frequency range. Although the effect of particle size and air-to-fuel ratio are inter-related, the predominant effect of air-to-fuel ratio is to determine the low frequency limit of the sound speed to be measured and the predominate effect of particle size is to determine the frequency range of the transitional regions. As particle size increases, the frequency at which the dispersive properties appear decreases. For typical pulverized coal applications, this transitional region begins at fairly low frequencies, ~2 Hz for 50 µm size particles.

Given the difficulties measuring sufficiently low frequencies to apply the quasi-steady model and recognizing that the high frequency sound speed contains no direct information on either particle size or air-to-fuel ratio, it becomes apparent that the dispersive characteristics of the coal/air mixture should be utilized to determine particle size and air-to-fuel ratio based on speed of sound measurements.

Some or all of the functions within the processing unit 24 may be implemented in software (using a microprocessor or computer) and/or firmware, or may be implemented using analog and/or digital hardware, having sufficient memory, interfaces, and capacity to perform the functions described herein.

While data acquisition units 40,54, FFT logic 42,56, data accumulators 44,58, array processors 46,60 and ridge identifiers 48, 62 are shown as separate elements or separate software/processing routines, one will appreciate that each of these elements may be common and able to process the data associated with both the pressure signals associated with the speed of sound and the pressures that convect with the process flow.

As shown in FIG. 1, the measurement apparatus 10 includes a sensing device 16 comprising an array of ultrasonic sensor units 22-25. Each sensor unit comprises a pair of ultrasonic sensors 40,42, one of which functions as a transmitter (Tx) 40 and the other as a receiver (Rx) 42. The sensor units 22-25 are spaced axially along the outer surface 17 of the pipe 14 having a process flow 12 propagating therein. The pair of sensors 40,42 is diametrically disposed on the pipe at predetermined locations along the pipe to provide a through transmission configuration, such that the sensors transmit and receive an ultrasonic signal that propagates through the fluid substantially orthogonal to the direction of the flow of the fluid within the pipe. The ultrasonic measurement portion of the present invention is similar to that shown in U.S. patent application Ser. No. 10/756,977 filed on Jan. 13, 2004, which is incorporated herein by reference.

As shown in FIG. 1, each pair of ultrasonic sensors 40,42 measures a transit time (i.e., time of flight (TOF), or phase modulation) of an ultrasonic signal propagating through the fluid 12 from the transmitting sensor 40 to the receiving sensor 42. The transit time measurement or variation is indicative of a coherent properties that convect with the flow within the pipe (e.g., vortical disturbances, inhomogenieties within the flow, temperature variations, bubbles, particles, pressure disturbances), which are indicative of the velocity of the process flow 12. The ultrasonic sensors may operate at any frequency, however, it has been found that the higher frequency sensors are more suitable for single phase fluids while lower frequency sensors are more suitable for multiphase fluids. The optimum frequency of the ultrasonic sensor is dependent on the size or type of particle or substance propagating with the flow 12. For instance, the larger the air bubbles in an aerated fluid the lower the desirable frequency of the ultrasonic signal. Examples of frequency used for a flow meter embodying the present invention are 1 MHz and 5 MHz. The ultrasonic sensors may also provide a pulsed, chirped or continuous signal through the fluid flow 12. An example of the sensors 40,42 that may be used are Model no. 113-241-591, manufactured by Krautkramer.

An ultrasonic signal processor 37 fires the sensors 40 in response to a firing signal 39 from the transmitter 24 and receives the ultrasonic output signals $S_1(t)$-$S_N(t)$ from the sensors 42. The signal processor 37 processes the data from each of the sensor units 18-21 to provide an analog or digital output signal $T_1(t)$-$T_N(t)$ indicative of the time of flight or transit time of the ultrasonic signal through the fluid. The signal processor 37 may also provide an output signal indicative of the amplitude (or attenuation) of the ultrasonic signals. One such signal processor is model no. USPC 2100 manufactured by Krautkramer Ultrasonic Systems. Measuring the amplitude of ultrasonic signal is particularly useful and works best for measuring the velocity of a fluid that includes a substance in the flow (e.g., multiphase fluid or slurry).

The output signals ($T_1(t)$-$T_N(t)$) of the ultrasonic signal processor 37 are provided to the processor 24, which processes the transit time measurement data to determine the volumetric flow rate. The transit time or time of flight measurement is defined by the time it takes for an ultrasonic signal to propagate from the transmitting sensor 40 to the respective receiving sensor 42 through the pipe wall and the fluid 12. The effect of the vortical disturbances (and/or other inhomogenities within the fluid) on the transit time of the ultrasonic signal is to delay or speed up the transit time. Therefore, each sensing unit 22-25 provides a respective output signal $T_1(t)$-$T_N(t)$ indicative of the variations in the transit time of the ultrasonic signals propagating orthogonal to the direction of the fluid 12. The measurement is derived by interpreting the convecting coherent property and/or characteristic within the process piping using at least two sensor units 22,23. The ultrasonic sensors 22-25 may be "wetted" or clamped onto the outer surface 17 of the pipe 14 (e.g. contact or non-contact sensor).

In one example, the flow meter 10 measures the volumetric flow rate by determining the velocity of vortical disturbances or "eddies" 88 (see FIG. 2) propagating with the flow 12 using the array of ultrasonic sensors 22-25. The flow meter 10 measures the velocities associated with unsteady flow fields created by vortical disturbances or "eddies" 88 and other inhomogenities to determine the velocity of the flow 12. The ultrasonic sensor units 22-25 measure the transmit time $T_1(t)$-$T_N(t)$ of the respective ultrasonic signals between each respective pair of sensors 40,42, which vary due to the vortical disturbances as these disturbances convect within the flow 12 through the pipe 14 in a known manner. Therefore, the velocity of these vortical disturbances is related to the velocity of the flow 12 and hence the volumetric flow rate may be determined, as will be described in greater detail hereinafter. The volumetric flow is determined by multiplying the velocity of the fluid by the cross-sectional area of the pipe.

The Flow Logic 65 processes the ultrasonic signals in a substantially similar way as that described for the Flow Logic 32 for the pressure signals shown in FIG. 3. Consequently, the pressure signals and the ultrasonic signals may be processed using a single processor to perform the Flow Logic 32 and the Flow Logic 65 or may be separate processors to enable simultaneous processing of the pressure and ultrasonic signals.

While each of the ultrasonic sensor units 22-25 of FIG. 1 comprises a pair of ultrasonic sensors (transmitter and receiver) 40,42 diametrically-opposed to provide through transmission, the present invention contemplates that one of the ultrasonic sensors 40,42 of each sensor unit 22-25 may be offset axially such that the ultrasonic signal from the transmitter sensor has an axial component in its propagation direction.

The present invention also contemplates the sensor units 22-25 of the sensing device 16 may be configured in a pulse/echo configuration. In this embodiment, each sensing unit 22-25 comprises one ultrasonic sensor that transmits an ultrasonic signal through the pipe wall and fluid substantially orthogonal to the direction of flow and receives a reflection of the ultrasonic signal reflected back from the wall of the pipe to the ultrasonic sensor.

The sensing device 16 may be configured to function in a pitch and catch configuration. In this embodiment, each sensor unit 22-25 comprises a pair of ultrasonic sensors (transmitter, receiver) 40, 42 disposed axially along the pipe disposed on the same side of the pipe at a predetermined distance apart. Each transmitter sensor 40 provides an ultrasonic signal a predetermined angle into the flow 12. The ultrasonic signal propagates through the fluid 12 and reflects off the inner surface of the pipe 14 and reflects the ultrasonic signal back through the fluid to the respective receiver sensor 42.

Figure 10:
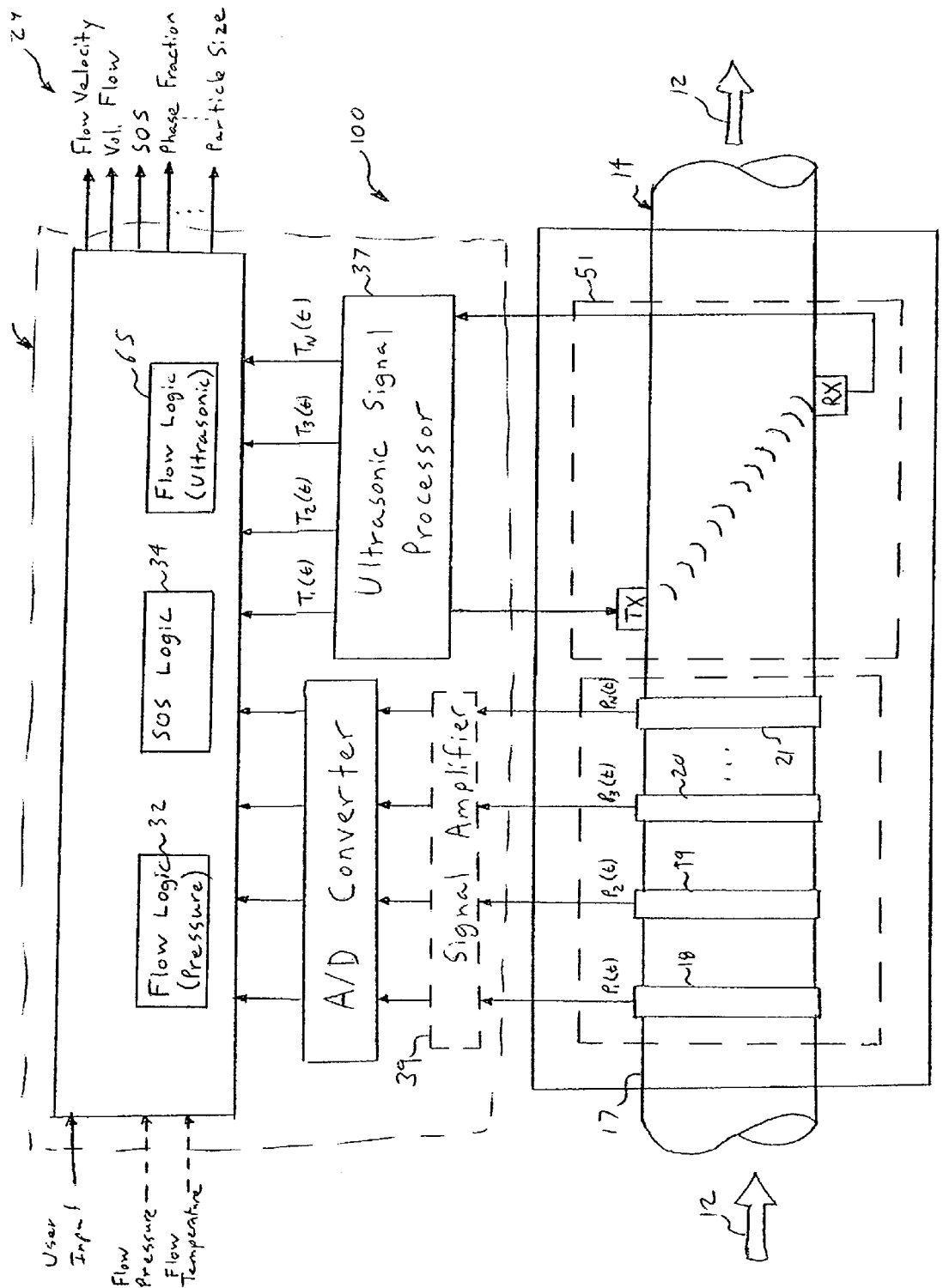
FIG. 10 is a schematic diagram of another embodiment of a flow measurement apparatus having an ultrasonic sensor and an array of strain-based sensors for providing a dual function in accordance with the present invention.

As shown in FIG. 10, while the ultrasonic sensor portion 51 comprises an array of ultrasonic sensor units 22-25 (see FIG. 1), the present invention contemplates that any ultrasonic meter or sensing portion may be used. The ultrasonic meter may be any meter within any of the three classes of flow meters that utilize ultrasonic transducers, which include transit time ultrasonic flow meters (TTUF), doppler ultrasonic flow meters (DUF), and cross correlation ultrasonic flow meters (CCUF). A transit time ultrasonic meter is illustrated in FIG. 10.

The ultrasonic sensor portion may be any known ultrasonic flow meter, such as U.S. Pat. Nos. 2,874,568; 4,004, 461; 6,532,827; 4,195,517; 5,856,622; and 6,397,683, which are all incorporated herein by reference.

The array-based flow meter is similar to that described in U.S. patent application Ser. No. 10/007,749 filed Nov. 7, 2001, U.S. patent application Ser. No. 10/007,736 filed Nov. 8, 2001, U.S. Pat. No. 6,587,798, filed on Nov. 28, 2001, U.S. Provisional Patent Application Ser. No. 60/359,785 filed Feb. 26, 2002. U.S. Provisional Patent Application Ser. No. 60/425,436 filed Nov. 12, 2002, U.S. patent application Ser. No. 09/729,994, filed Dec. 4, 2000, and U.S. patent application, Ser. No. 10,875,857 filed Jun. 24, 2004, which are all incorporated herein by reference.

While a single array processor 32 is shown to receive and process input signals from the pressure sensors 18-21 and the ultrasonic sensors 22-25, the present invention contemplates that an array processor may be dedicated to each of the array of pressure sensor 18-21 and the array of ultra-sonic sensors 22-25.

In one embodiment as shown in FIG. 1, each of the pressure sensors 18-21 may include a piezoelectric film 50 attached to a unitary multi-band strap 52 to measure the unsteady pressures of the flow 12 using either technique described hereinbefore. The piezoelectric film sensors 18-21 are mounted onto a unitary substrate or web which is mounted or clamped onto the outer surface 22 of the pipe 14, which will be described in greater detail hereinafter.

The piezoelectric film sensors 18-21 include a piezoelectric material or film 50 to generate an electrical signal proportional to the degree that the material is mechanically deformed or stressed. The piezoelectric sensing element 50 is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc. While the piezoelectric film material 50 is substantially the length of the band 44, and therefore the circumference of the pipe 14, the present invention contemplates that the piezoelectric film material may be disposed along a portion of the band of any length Less than the circumference of the pipe.

Piezoelectric film ("piezofilm") 50, like piezoelectric material, is a dynamic material that develops an electrical charge proportional to a change in mechanical stress. Consequently, the piezoelectric material measures the strain induced within the pipe 14 due to unsteady or stochastic pressure variations (e.g., vortical and/or acoustical) within the process flow 12. Strain within the pipe is transduced to an output voltage or current by the attached piezoelectric sensor 18-21. The piezoelectrical material or film 50 may be formed of a polymer, such as polarized fluoropolymer, polyvinylidene fluoride (PVDF). The piezoelectric film sensors are similar to that described in U.S. patent application Ser. No. 10/712,818, filed Nov. 12, 2003 and U.S. patent application Ser. No. 10/795,111, filed Mar. 4, 2004, which are incorporated herein by reference. The advantages of this clamp-on technique using piezoelectric film include non-intrusive flow rate measurements, low cost, measurement technique requires no excitation source. One will appreciate that the sensor may be installed or mounted to the pipe 14 as individual sensors or all the sensors mounted as a single unit as shown in FIG. 1.

The pressure sensors 18-21 of FIG. 1 described herein may be any type of sensor, capable of measuring the unsteady (or ac or dynamic) pressures or parameter that convects with the flow within a pipe 14, such as piezoelectric, optical, capacitive, resistive (e.g., Wheatstone bridge), accelerometers (or geophones), velocity measuring devices, displacement measuring devices, ultra-sonic devices, etc. If optical pressure sensors are used, the sensors 18-21 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application Ser. No. 10/224,821, entitled "Non-Intrusive Fiber Optic Pressure Sensor for Measuring Unsteady Pressures within a Pipe", which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 18-21 and it may measure the unsteady (or dynamic or ac) pressure variations inside the pipe 14 by measuring the pressure levels inside of the pipe. These sensors may be ported within the pipe to make direct contact with the process flow 12. In an embodiment of the present invention, the sensors comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354, 147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the pipe, such as highly sensitive piezo-electric, electronic or electric, strain gages attached to or embedded in the pipe 14.

While the description has described the apparatus as two separate meters that measure the vortical disturbances and the speed of sound, respectively, as suggested by FIG. 1, the processing could function as two separate meters, a combination (simultaneous operation) of both function, or selectively choose between operations.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring a process flow flowing within a pipe, the apparatus comprising:
    at least two strain sensors disposed at different axial locations along the pipe, each of the strain sensors providing a respective pressure signal indicative of pressure disturbances within the pipe at the corresponding axial location;
    at least two ultrasonic sensors disposed along the pipe that provides an ultrasonic signal indicative of a parameter of the process flow, each ultrasonic sensor comprising a transmitter and a receiver, wherein each transmitter transmit an ultrasonic wave to the respective receiver such that the respective ultrasonic wave propagates substantially orthogonal to the direction of the process flow; and
    a signal processor, responsive to said pressure signals and ultrasonic signal, which provides a first signal indicative of a velocity of a pressure field moving with the process flow and/or provides a second signal indicative of a speed of sound propagating through the process flow.

2. The apparatus of claim 1, wherein the processing unit includes a convective processing unit that includes an array processor that determines power in the k-ω plane, the convective ridge in the k-ω plane, and a slope of the convective ridge to determine one of the velocity, the mach number, and volumetric flow rate of the process flow.

3. The apparatus of claim 1, wherein the processing unit includes an acoustic processing unit that includes an array processor that determines power in the k-ω plane and determines the acoustic ridge in the k-ω plane.

4. The apparatus of claim 1, wherein the pressure signals are indication of acoustic pressures propagating axially within the flow and unsteady pressures convecting with the flow.

5. The apparatus of claim 1, wherein the at least two pressure sensors include one of 3, 4, 5, 6, 7, 8, 9, 10, 11, 12, 13, 14, 15, 16, 17, 18, 19 and 20 pressure sensors.

6. The apparatus of claim 1, wherein the at least two ultrasonic sensors provides a respective signal indicative of a parameter of the ultrasonic wave propagating between each respective transmitter and receiver.

7. The apparatus of claim 6, wherein the processor samples the ultrasonic signals over a predetermined time period, accumulates the sampled ultrasonic signals over a predetermined sampling period, and processes the sampled ultrasonic signals to define the convective ridge in the k-ω plane.

8. The apparatus of claim 7, wherein the ultrasonic signals are indicative of vortical disturbances with the fluid.

9. The apparatus of claim 6, wherein the parameter of the ultrasonic signal is at least one of the signal amplitude and the signal transit time of an ultrasonic signal.

10. The apparatus of claim 6, wherein the at least two ultrasonic sensor units include one of 3, 4, 5, 6, 7, 8, 9, 10, 11, 12, 13, 14, 15, 16, 17, 18, 19 and 20 ultrasonic sensors.

11. The apparatus of claim 10, wherein the signal processor defines a convective ridge in the k-ω plane in response to the ultrasonic signals, and determines the slope of at least a portion of the convective ridge to determine the flow velocity of the fluid.

12. The apparatus of claim 1, wherein the signal processor in response to an environmental condition provides one of a first output signal, responsive to the first signal, or a second output signal, responsive to the second signal.

13. The apparatus of claim 12, wherein the environmental condition is vibration on the pipe.

14. The apparatus of claim 1, wherein the signal processor in response to a user input signal provides one of a first output signal, responsive to the first signal, or a second output signal, responsive to the second signal.

15. An apparatus for measuring a process flow flowing within a pipe, the apparatus comprising:
    at least two strain sensors disposed at different axial locations along the pipe, each of the strain sensors providing a respective pressure signal indicative of pressure disturbances within the pipe at the corresponding axial location;
    at least two ultrasonic sensors disposed along the pipe that provides an ultrasonic signal indicative of a parameter of the process flow, each ultrasonic sensor comprising a transmitter and a receiver, wherein each transmitter transmit an ultrasonic wave to the respective receiver such that the respective ultrasonic wave propagates substantially orthogonal to the direction of the process flow; and
    a signal processor which, responsive to said ultrasonic signal, provides a first signal indicative of a velocity of the process flow; and which, responsive to said pressure signals, provides a second signal indicative of a velocity of a pressure field moving with the process flow and/or a third signal indicative of the speed of sound propagating axially through the process flow.

16. The apparatus of claim 15, wherein the processing unit includes a convective processing unit that includes an array processor that determines power in the k-ω plane, the convective ridge in the k-ω plane, and a slope of the convective ridge to determine one of the velocity, the mach number, and volumetric flow rate of the process flow.

17. The apparatus of claim 15, wherein the processing unit includes an acoustic processing unit that includes an array processor that determines power in the k-ω plane and determines the acoustic ridge in the k-ω plane.

18. The apparatus of claim 15, wherein the pressure signals are indication of acoustic pressures propagating axially within the flow and unsteady pressures convecting with the flow.

19. The apparatus of claim 15, wherein the at least two pressure sensors include one of 3, 4, 5, 6, 7, 8, 9, 10, 11, 12, 13, 14, 15, 16, 17, 18, 19 and 20 pressure sensors.

20. The apparatus of claim 15, wherein the at least two ultrasonic sensors provide a respective signal indicative of a parameter of an ultrasonic signal propagating between each respective ultrasonic transmitter and ultrasonic receiver.

21. The apparatus of claim 20, wherein the signal processor samples the ultrasonic signals over a predetermined time period, accumulates the sampled ultrasonic signals over a predetermined sampling period, and processes the sampled ultrasonic signals to define the convective ridge in the k-ω plane.

22. The apparatus of claim 21, wherein the ultrasonic signals are indicative of vortical disturbances with the fluid.

23. The apparatus of claim 15, wherein the parameter of the ultrasonic signal is at least one of the signal amplitude and the signal transit time of an ultrasonic signal.

24. The apparatus of claim 15, wherein the at least two ultrasonic sensor units include one of 3, 4, 5, 6, 7, 8, 9, 10, 11, 12, 13, 14, 15, 16, 17, 18, 19 and 20 ultrasonic sensors.

25. The apparatus of claim 24, wherein the signal processor defines a convective ridge in the k-ω plane in response to the ultrasonic signals, and determines the slope of at least a portion of the convective ridge to determine the flow velocity of the fluid.

26. The apparatus of claim 15, wherein the signal processor in response to an environmental condition provides one of a first output signal, responsive to the first signal, or a second output signal, responsive to the second signal.

27. The apparatus of claim 26, wherein the environmental condition is vibration on the pipe.

28. The apparatus of claim 15, wherein the signal processor in response to a user input signal provides one of a first output signal, responsive to the first signal, or a second output signal, responsive to the second signal.

* * * * *